United States Patent
Wei et al.

(10) Patent No.: US 9,220,701 B2
(45) Date of Patent: Dec. 29, 2015

(54) STABILIZED COMPOSITION FOR TREATING PSORIASIS

(75) Inventors: William Shifeng Wei, Belle Mead, NJ (US); Yiping Wang, Howell, NJ (US); Jianzhen Pan, Monroe, NJ (US); Sung Hi Jo, Philadelphia, PA (US)

(73) Assignee: NEXMED HOLDINGS, INC., San Diego, CA (US)

( * ) Notice: Subject to any disclaimer, the term of this patent is extended or adjusted under 35 U.S.C. 154(b) by 176 days.

(21) Appl. No.: 12/998,261

(22) PCT Filed: Oct. 2, 2009

(86) PCT No.: PCT/US2009/005426
§ 371 (c)(1),
(2), (4) Date: Jun. 1, 2011

(87) PCT Pub. No.: WO2010/039251
PCT Pub. Date: Apr. 8, 2010

(65) Prior Publication Data
US 2011/0237558 A1    Sep. 29, 2011

Related U.S. Application Data

(60) Provisional application No. 61/195,126, filed on Oct. 3, 2008.

(51) Int. Cl.
| | | |
|---|---|---|
| *A01N 45/00* | (2006.01) | |
| *A61K 31/59* | (2006.01) | |
| *A61K 31/221* | (2006.01) | |
| *A61K 31/355* | (2006.01) | |
| *A61K 31/58* | (2006.01) | |
| *A61K 9/00* | (2006.01) | |
| *A61K 47/06* | (2006.01) | |
| *A61K 47/18* | (2006.01) | |
| *A61K 9/06* | (2006.01) | |

(52) U.S. Cl.
CPC ............. *A61K 31/221* (2013.01); *A61K 9/0014* (2013.01); *A61K 9/06* (2013.01); *A61K 31/355* (2013.01); *A61K 31/58* (2013.01); *A61K 31/59* (2013.01); *A61K 47/06* (2013.01); *A61K 47/18* (2013.01)

(58) Field of Classification Search
USPC .................................................. 514/168, 167
See application file for complete search history.

(56) References Cited

U.S. PATENT DOCUMENTS

| | | |
|---|---|---|
| 4,980,378 A | 12/1990 | Wong et al. |
| 2005/0281755 A1 | 12/2005 | Zarif et al. |
| 2006/0057075 A1 | 3/2006 | Arkin et al. |
| 2006/0067898 A1 | 3/2006 | Kepka et al. |
| 2006/0292080 A1 | 12/2006 | Abram et al. |
| 2008/0069779 A1 | 3/2008 | Tamarkin et al. |

FOREIGN PATENT DOCUMENTS

| | | |
|---|---|---|
| CN | 1449270 A | 10/2003 |
| EP | 1 140 021 B1 | 8/2004 |
| WO | WO-99/22714 A1 | 5/1999 |
| WO | WO-00/38653 A1 | 7/2000 |
| WO | WO 00/64450 A1 | 11/2000 |
| WO | WO-01/74279 A1 | 10/2001 |
| WO | WO-2004/054588 A1 | 7/2004 |
| WO | WO-2004/084826 A2 | 10/2004 |
| WO | WO-2007/070643 A2 | 6/2007 |
| WO | WO-2008/045309 A1 | 4/2008 |

OTHER PUBLICATIONS

Taclonex® web information package (Oct. 17, 2007).*
Simonsen et. al. (Drug Development and Industrial Pharmacy (2004) 30:1095-1102).*
Buyuktimkin et. al. (Percutaneous Penetration Enhancers, Edited by E. W. Smith and H. I. Maibach, CRC Press (1995), Chapter 4.2 pp. 91-102).*
Kaufmann et al., "A New Calsipotriol/Betamethasone Dipropionate Formulation (Daivobet™) Is an Effective Once-Daily Treatment for Psoriasis vulgaris," Dermatology, (2002), 205:389-393.
Kragballe et al., "Calcipotriol cream with or without concurrent topical corticosteroid in psoriasis: tolerability and efficacy," British Journal of Dermatology, (1998), 139:649-654.
International Search Report and Written Opinion for PCT Patent Application No. PCT/US2009/005426 issued Dec. 1, 2009.
Technical information of TACLONEX®, approved by FDA in 2006, http://www.taclonex.com/pdf/Taclonex_topical_USPI.pdf.
MX Office Action for Appl. No. MX/a/2011/003568, dated Jan. 27, 2015.

* cited by examiner

*Primary Examiner* — Marcos Sznaidman
(74) *Attorney, Agent, or Firm* — Foley & Lardner LLP

(57) ABSTRACT

A storage stable ointment of the present invention comprises a vitamin D compound, a corticosteroid, and an N,N-di ($C_1$-$C_8$)alkylamino substituted, ($C_4$-$C_{18}$)alkyl($C_2$-$C_{18}$)carboxylic ester a ($C_1$-$C_4$)-alkyl($C_8$-$C_{22}$)carboxylic ester in a petrolatum ointment base, and optionally containing mineral oil and/or tocopherol. Preferably, the vitamin D compound is calcipotriene, the corticosteroid is selected from the group consisting of clobetasol propionate and betamethasone dipropionate, and the N,N-di($C_1$-$C_8$) alkylamino substituted, ($C_4$-$C_{18}$)alkyl ($C_2$-$C_{18}$) carboxylic ester comprises dodecyl 2-(N,N-dimethylamino)-propionate (DDAIP).

25 Claims, 2 Drawing Sheets

STABILIZED COMPOSITION FOR TREATING PSORIASIS

CROSS-REFERENCE TO RELATED APPLICATIONS

This application is the U.S. national stage application of International Patent Application No. PCT/US2009/005426, filed on Oct. 2, 2009, which claims priority to U.S. Provisional Application No. 61/195,126, filed on Oct. 3, 2008, each of which are incorporated herein by reference in their entirety.

TECHNICAL FIELD

This application relates to room temperature-stable, non-aqueous ointment compositions containing a vitamin D compound and a corticosteroid useful for treating psoriasis.

BACKGROUND OF THE INVENTION

Psoriasis is a noncontagious disease that affects the skin and joints. The disease is accompanied by red scaly patches on the skin, called psoriatic plaques, which are areas of inflammation and excessive skin production. As many as 7.5 million Americans have psoriasis, according to the National Institutes of Health. It has been estimated that about 10 percent to 30 percent of people with psoriasis will also develop a joint disease known as psoriatic arthritis, which causes joint pain, stiffness and swelling.

Psoriasis is a chronic recurring condition, which can vary significantly in severity. Some sufferers exhibit minor localised patches of psoriatic plaques, while others have plaque overage over almost every area of the body. Fingernails and toenails are often affected.

The cause of psoriasis is not known, but it may have a genetic component. Stress, excessive alcohol consumption, and smoking have been known to aggravate the condition. In addition to the obvious physical manifestations, individuals with psoriasis may also suffer from depression and loss of self-esteem.

There are many topical medications that have been utilized to treat psoriasis. For example, vitamin D-3 (calcipotriene), coal tar, corticosteroids (e.g., clobetasol, fluocinolone, and betamethasone), tree bark extract (e.g., anthralin), and retinoids (e.g., tazarotene). Compositions for treating psoriasis that include both vitamin D compounds and corticosteroids have also been described (see U.S. Pat. No. 6,753,013). Combinations of vitamin D compounds and corticosteroids can be unstable, since the corticosteroids tend to favor acidic conditions, whereas vitamin D compounds are more stable in alkaline conditions. TACLONEX® topical ointment is a combination product, which includes both calcipotriene and betamethasone dipropionate, and is stabilized by a polyoxyalkylene ether-type solvent.

SUMMARY OF THE INVENTION

A storage stable ointment of the present invention comprises a vitamin D compound, a corticosteroid, and an N,N-di($C_1$-$C_8$)alkylamino substituted, ($C_4$-$C_{18}$)alkyl($C_2$-$C_{18}$)carboxylic ester a ($C_1$-$C_4$)-alkyl($C_8$-$C_{22}$)carboxylic ester, in a petrolatum carrier, and optionally containing mineral oil, tocopherol, or both. Preferably, the vitamin D compound comprises calcipotriene. The corticosteroid preferably is a pharmaceutically acceptable salt of clobetasol or a pharmaceutical acceptable salt of betamethasone. A preferred N,N-di($C_1$-$C_8$)alkylamino substituted, ($C_4$-$C_{18}$)alkyl($C_2$-$C_{18}$)carboxylic ester is dodecyl 2-(N,N-dimethylamino)-propionate (DDAIP).

The compositions of the present invention have storage stabilities comparable to commercial TACLONEX® topical ointment, while providing for surprisingly enhanced skin penetration of calcipotriene compared to the commercial product.

Figure 1:
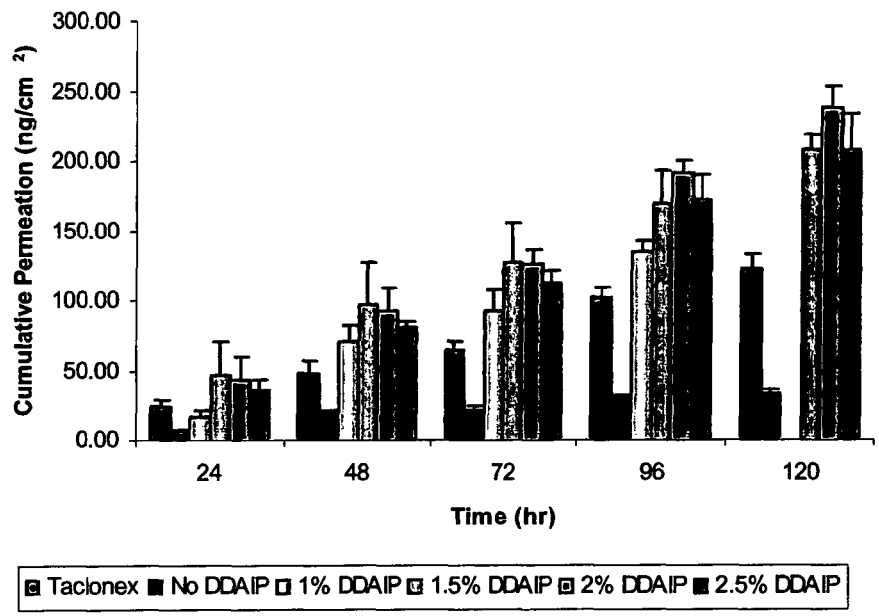
FIG. 1 depicts a graph of cumulative permeation of calcipotriene through pig ear skin versus time on the skin from a standard assay of skin permeation performed on compositions of the present invention containing calcipotriene, betamethasone dipropionate, and various amounts of DDAIP, compared to a composition containing no DDAIP, and TACLONEX® ointment.

In the graphs of FIGS. 1, 2, 3, and 4, the bars in each time group in each graph are arranged in the order shown in the key below each graph.

DESCRIPTION OF PREFERRED EMBODIMENTS

The present invention provides a storage stable ointment useful for treatment of psoriasis. The compositions of the invention comprise a vitamin D compound, a corticosteroid, and an N,N-di($C_1$-$C_8$)alkylamino substituted, ($C_4$-$C_{18}$)alkyl ($C_2$-$C_{18}$) carboxylic ester a ($C_1$-$C_4$)-alkyl($C_8$-$C_{22}$)carboxylic ester, in a petrolatum (e.g., white petrolatum) carrier, and optionally containing mineral oil, tocopherol (vitamin E), or both mineral oil and tocopherol.

Suitable vitamin D compounds for use in the compositions of the present invention include calcipotriene (also known as calcipotriol), calcitriol, tacalcitol, maxacalcitol, and 1(S),3(R)-dihydroxy-20(R)-[((3(2-hydroxy-2-propyl)-phenyl)-methoxy)-methyl]-9,10-seco-pregna-5(Z),7(E),10(19)-triene, as well as combinations of two or more thereof. A preferred vitamin D compound is calcipotriene, which is (1R,3S)-5-[2-[(1R,3aR,7aS)-1-[(2S)-5-cyclopropyl-5-hydroxy-pent-3-en-2-yl]-7a-methyl-2,3,3a,5,6,7-hexahydro-1H-inden-4-ylidene]ethylidene]-4-methylidene-cyclohexane-1,3-diol (IUPAC name), preferably as the monohydrate. The vitamin D compound preferably is present in the composition at a concentration in the range of about 0.001 to about 0.01 percent by weight.

Suitable corticosteroids for use in the compositions of the present invention include hydrocortisone, desonide, flumethasone pivalate, fluocinolone acetonide, triamcinolone acetonide, alclometasone dipropionate, hydrocortisone valerate, prednicarbate, clocortolone pivalate, fluticasone propionate, mometasone furoate, betamethasone, betamethasone dipropionate, amcinonide, desoximetasone, diflorason, fluocinonide, halcinonide, halobetasol propionate, clobetasol propionate, and combinations of two or more thereof. Particularly preferred corticosteroids are clobetasol propionate and betamethasone dipropionate. Preferably, the corticosteroid is present in the composition at a concentration in the range of about 0.01 to about 0.1 percent by weight.

Tocopherol is also preferably included in the compositions of the present invention, e.g., at a concentration in the range of about 0.001 to 0.01 percent by weight.

In addition, the compositions of the present invention include a N,N-di($C_1$-$C_8$)alkylamino substituted, ($C_4$-$C_{18}$) alkyl($C_2$-$C_{18}$)carboxylic ester, e.g., as a solvent and a skin penetration enhancer, preferably at a concentration in the range of about 0.1 to about 5 percent by weight. The term "N,N-di($C_1$-$C_8$)alkylamino substituted," in reference to a ($C_4$-$C_{18}$)alkyl($C_2$-$C_{18}$)carboxylic ester means that either the alcohol portion or the carboxylic acid portion from which the ester is prepared bears an amino substituent $NR_xR_y$, wherein $R_x$ and $R_y$ are each independently a ($C_1$-$C_8$)alkyl group. Preferably $R_x$ and $R_y$ are both methyl groups. Examples of suitable such compounds include dodecyl-2-(N,N-dimethylamino)-propionate (DDAIP); dodecyl-2-(N,N-dimethylamino)-acetate (DDAA); 1-(N,N-dimethylamino)-2-propyl dodecanoate (DAIPD); and 1-(N,N-dimethylamino)-2-propyl myristate (DAIPM); 1-(N,N-dimethylamino)-2-propyl oleate (DAIPO). The preparation of DDAIP and crystalline acid addition salts thereof is described in U.S. Pat. No. 6,118,020 to Büyüktimkin, et al., which is incorporated herein by reference in its entirety. Long chain similar amino substituted, alkyl carboxylic esters can be synthesized from readily available compounds as described in U.S. Pat. No. 4,980,378 to Wong, et al., which is incorporated herein by reference to the extent that it is not inconsistent herewith. A preferred N,N-di($C_1$-$C_8$)alkylamino substituted, ($C_4$-$C_{18}$)alkyl($C_2$-$C_{18}$)carboxylic ester is DDAIP.

The compositions of the present invention can include up to about 10 percent by weight (e.g., 1 to 10 percent) of mineral oil. Preferably, the composition includes about 1 to about 5 percent by weight of mineral oil.

In a preferred embodiment, a composition of the invention comprises about 0.001 to about 0.01 percent by weight of a vitamin D compound; about 0.01 to about 0.1 percent by weight of a corticosteroid; about 0.001 to about 0.01 percent by weight of tocopherol; and about 0.1 to about 5 percent by weight of an N,N-di($C_1$-$C_8$)alkylamino substituted, ($C_4$-$C_{18}$) alkyl($C_2$-$C_{18}$)carboxylic ester a ($C_1$-$C_4$)-alkyl($C_8$-$C_{22}$)carboxylic ester; in a petrolatum carrier, and optionally contains mineral oil.

In particularly preferred embodiments, the vitamin D compound comprises calcipotriene, the corticosteroid is selected from the group consisting of clobetasol propionate and betamethasone dipropionate, and the N,N-di($C_1$-$C_8$)alkylamino substituted, ($C_4$-$C_{18}$) alkyl($C_2$-$C_{18}$)carboxylic ester is DDAIP, CAS Reg. No. 224297-43-2. One such preferred embodiment comprises about 0.001 to about 0.01 percent by weight of a calcipotriene; about 0.01 to about 0.1 percent by weight of a corticosteroid selected from clobetasol propionate and betamethasone dipropionate; about 0.001 to about 0.01 percent by weight of tocopherol; up to about 10 percent by weight mineral oil, and about 0.1 to about 5 percent by weight of an N,N-di($C_1$-$C_8$)alkylamino substituted, ($C_4$-$C_{18}$) alkyl($C_2$-$C_{18}$)carboxylic ester a ($C_1$-$C_4$)-alkyl($C_8$-$C_{22}$)carboxylic ester; in a petrolatum carrier.

The following non-limiting Examples are provided to illustrate certain aspects and features of the present invention.

EXAMPLE 1

Two compositions of the present invention were prepared. The formulations of the compositions are described in Tables 1 and 2. In Tables 1 and 2, and subsequent tables, "CAL" refers to calcipotriene; "BET-D" refers to betamethasone dipropionate; and "CLO-P" refers to clobetasol propionate.

TABLE 1

| Comp. 1 | | | | | |
|---|---|---|---|---|---|
| CAL | BET-D | DDAIP | Vitamin E | Mineral Oil | White Petrolatum |
| 0.005% | 0.064% | 1% | 0.002% | 3% | q.s. 100 |

TABLE 2

| Comp. 2 | | | | | |
|---|---|---|---|---|---|
| CAL | CLO-P | DDAIP | Vitamin E | Mineral Oil | White Petrolatum |
| 0.005% | 0.05% | 1% | 0.002% | 3% | q.s. 100 |

EXAMPLE 2

Stability data of the combination compositions of Example 1 are described in Table 3. The reference standard was TACLONEX® ointment (a commercial product containing calcipotriene and betamethasone dipropionate, stabilized with a poly(alkylene oxide) ester solvent), which is known to be a stable product. The compositions of Example 1 and TACLONEX® ointment were stored at the indicated temperatures show in Table 3, and analyzed by high performance liquid chromatography for the indicated API (active pharmaceutical ingredient). The number entries in Table 3 are percentages of the indicated active ingredient based on the known formulations of the compositions, from analyses of samples taken at the indicated the storage times and temperatures.

TABLE 3

| | | 25° C. | | 40° C. | | | |
|---|---|---|---|---|---|---|---|
| Formulation | API | Initial | 4 wk | Initial | 1 wk | 2 wk | 4 wk |
| TALCONEX ® | CAL | | | 89.92 | 96.94 | 100.23 | 98.78 |
| | BET-D | | | 104.33 | 104.66 | 104.63 | 105.57 |
| Comp. 1 | CAL | 103.72 | 105.32 | 103.72 | 104.79 | 100.4 | 106.61 |
| | BET-D | 99.50 | 99.84 | 99.50 | 98.68 | 94.77 | 99.75 |

TABLE 3-continued

|  |  | 25° C. | | 40° C. | | | |
| --- | --- | --- | --- | --- | --- | --- | --- |
| Formulation | API | Initial | 4 wk | Initial | 1 wk | 2 wk | 4 wk |
| Comp. 2 | CAL | 99.57 | 99.58 | 99.57 | 101.44 | 106.08 | 106.23 |
|  | CLO-P | 99.78 | 98.64 | 99.78 | 100.86 | 95.92 | 102.21 |

The data in Table 3 clearly demonstrate that the compositions of the present invention have storage stabilities comparable to the commercial reference product.

EXAMPLE 3

Figure 2:
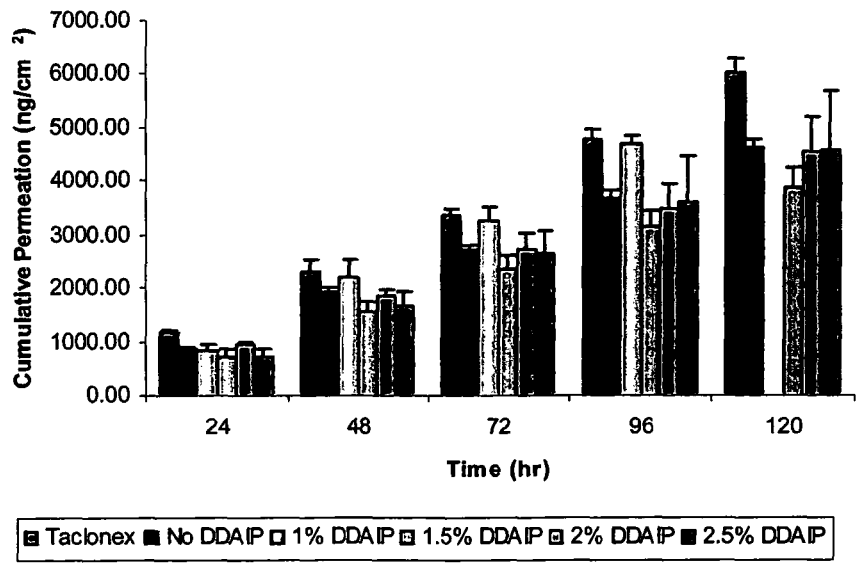
FIG. 2 depicts a graph of cumulative permeation of betamethasone through pig ear skin versus time on the skin from a standard assay of skin permeation performed on compositions of the present invention containing calcipotriene, betamethasone dipropionate, and various amounts of DDAIP, compared to a composition containing no DDAIP, and TACLONEX® ointment.
Figure 3:
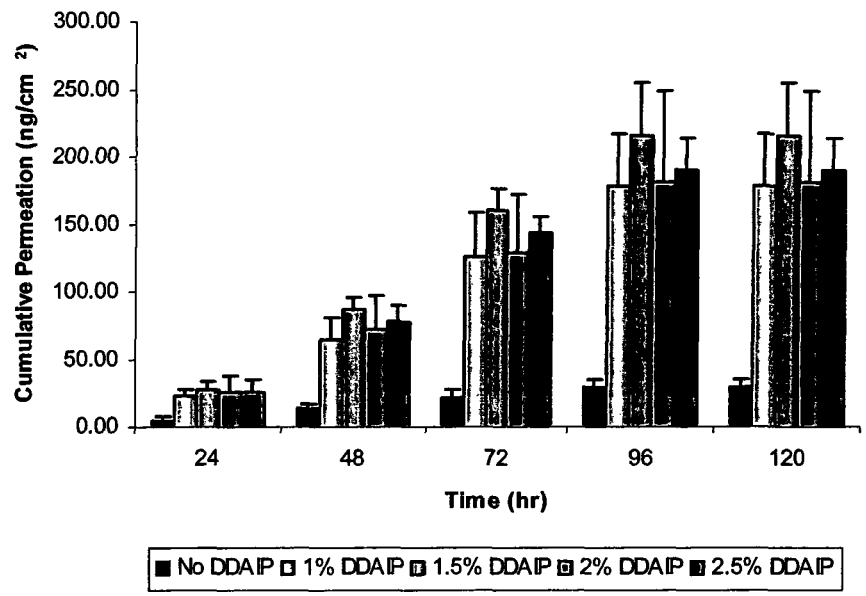
FIG. 3 depicts a graph of cumulative permeation of calcipotriene through pig ear skin versus time on the skin from a standard assay of skin permeation performed on compositions of the present invention containing calcipotriene, clobetasol propionate, and various amounts of DDAIP, compared to a composition containing no DDAIP.
Figure 4:
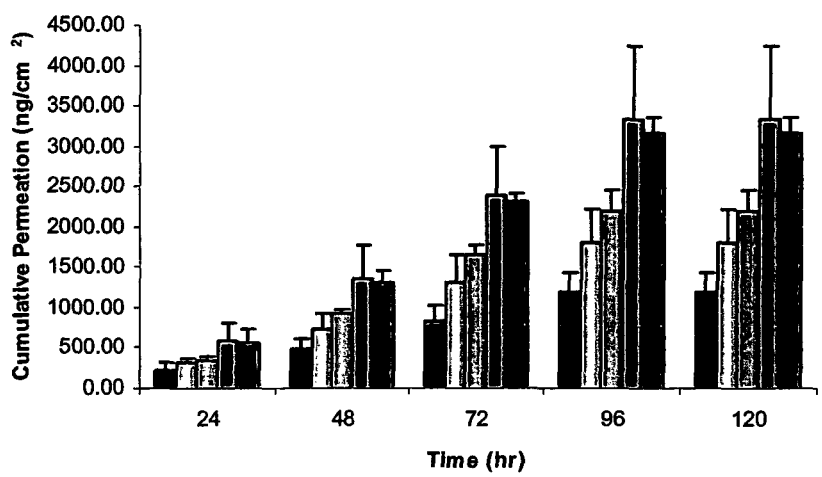
FIG. 4 depicts a graph of cumulative permeation of clobetasol through pig ear skin versus time on the skin from a standard assay of skin permeation performed on compositions of the present invention containing calcipotriene, clobetasol propionate, and various amounts of DDAIP, compared to a composition containing no DDAIP.

Compositions of the invention were also evaluated for their permeation through pig ear skin. Pig ear skin is commonly used to evaluate the permeation of topical products due to its permeation proximity to that of human skin. Compositions of the invention containing 0.005 wt. % calcipotriene, 0.002 wt. % tocopherol, 3 wt. % mineral oil, and either 0.05 wt. % clobetasol propionate or 0.064 wt. % betamethasone dipropionate, in a white petrolatum carrier, containing varying concentrations of DDAIP (1, 1.5, 2, and 2.5 wt. %) were examined, along with control composition containing no DDAIP, and TACLONEX® ointment. Penetration of calcipotriene, clobetasol, and betamethasone were evaluated. The results are shown in Tables 4 and 5, as well as in FIGS. 1, 2, 3, and 4. The numerical values in Tables 4 and 5, and in the figures are in units of nanograms of the analyte per square centimeter of skin (ng/cm$^2$). FIG. 1 depicts a graph of cumulative permeation of calcipotriene through pig ear skin versus the amount of time the composition was on the skin, for the calcipotriene/betamethasone-containing compositions and TACLONEX® ointment. FIG. 2 depicts a graph of cumulative permeation of betamethasone through pig ear skin versus the amount of time the compositions were on the skin for the calcipotriene/betamethasone-containing compositions, and TACLONEX® ointment. FIG. 3 depicts a graph of cumulative permeation of calcipotriene through pig ear skin versus the amount of time the compositions were on the skin for the calcipotriene/clobetasol-containing compositions. FIG. 4 depicts a graph of cumulative permeation of clobetasol through pig ear skin versus the amount of time the compositions were on the skin for the calcipotriene/clobetasol-containing compositions.

TABLE 4

| APIs | Time | TACLONEX | No DDAIP | 1% DDAIP | 1.5% DDAIP | 2% DDAIP | 2.5% DDAIP |
| --- | --- | --- | --- | --- | --- | --- | --- |
| CAL-P | 24 hrs | 23.95 | 6.82 | 15.94 | 47.01 | 42.87 | 35.49 |
|  | 48 hrs | 47.43 | 18.66 | 69.55 | 97.25 | 92.40 | 80.11 |
|  | 96 hrs | 101.62 | 29.13 | 134.29 | 168.62 | 191.46 | 172.08 |
|  | 120 hrs | 121.85 | 33.40 | NA | 207.99 | 236.98 | 207.97 |
| BET-D | 24 hrs | 1170.26 | 886.74 | 825.64 | 710.73 | 961.47 | 732.73 |
|  | 48 hrs | 2305.96 | 1911.06 | 2199.42 | 1547.33 | 1857.53 | 1672.54 |
|  | 96 hrs | 4769.36 | 3675.04 | 4678.47 | 3141.54 | 3493.81 | 3613.49 |
|  | 120 hrs | 6016.93 | 4608.58 | NA | 3856.93 | 4540.46 | 4569.25 |

The data in Table 4 and in FIGS. 1 and 2 clearly demonstrate that DDAIP at the 1.5-2.5% concentration range provided a surprising enhancing effect in calcipotriene permeation at all evaluation times compared to the composition with no DDAIP and to TACLONEX® ointment, which contains a poly(alkylene glycol) ester solvent. Similarly, composition containing 1% DDAIP also showed a surprising enhancement in calcipotriene penetration in the 24 to 96 hour evaluations compared to the composition with no DDAIP and to TACLONEX® ointment. The composition containing 2% DDAIP exhibited about 7.1 times higher calcipotriene penetration compared to the composition with no DDAIP, and 1.9 times higher penetration than TACLONEX® ointment.

TABLE 5

| APIs | Time | No DDAIP | 1% DDAIP | 1.5% DDAIP | 2% DDAIP | 2.5% DDAIP |
| --- | --- | --- | --- | --- | --- | --- |
| Calcipotriene | 24 hrs | 4.70 | 22.02 | 26.72 | 24.85 | 24.63 |
|  | 48 hrs | 12.73 | 64.70 | 86.37 | 71.07 | 77.02 |
|  | 96 hrs | 20.61 | 126.10 | 160.21 | 129.09 | 142.59 |
|  | 120 hrs | 27.82 | 177.36 | 215.60 | 180.32 | 189.47 |
| Clobetasol | 24 hrs | 216.65 | 308.81 | 333.98 | 594.61 | 563.00 |
| Propionate | 48 hrs | 479.48 | 740.02 | 917.70 | 1361.73 | 1319.23 |
|  | 96 hrs | 823.64 | 1312.23 | 1650.36 | 2389.20 | 2321.16 |
|  | 120 hrs | 1180.69 | 1799.70 | 2200.68 | 3323.45 | 3151.98 |

The data in Table 5 and in FIGS. 3 and 4 clearly demonstrate that DDAIP at the 1-2.5% concentration range provided a surprising enhancing effect in calcipotriene permeation at all evaluation times compared to the composition with no DDAIP, similar to the enhancement observed for the betamethasone compositions. The clobetasol permeation was also considerably enhanced by the presence of DDAIP. The presence of DDAIP at 2% provided a clobetasol permeation at 120 hours that was about 2.8 times higher than the clobetasol permeation observed for the composition that did not contain DDAIP. The presence of 1.5% DDAIP provided calcipotriene permeation at 120 hours that was about 7.7 times higher than the calcipotriene permeation observed for the composition containing no DDAIP.

The foregoing examples have been provided as an illustration of preferred embodiments of the invention, and are not meant to limit the scope of the invention.

We claim:

1. A storage stable non-aqueous ointment suitable for treating psoriasis comprising:
 (a) a vitamin D compound;
 (b) a corticosteroid; and
 (c) an N,N-di($C_1$-$C_8$)alkylamino substituted, ($C_4$-$C_{18}$) alkyl($C_2$-$C_{18}$)carboxylic ester;
 in a petrolatum carrier, and optionally containing mineral oil, tocopherol, or a combination of mineral oil and tocopherol.

2. The ointment of claim 1 wherein the vitamin D compound comprises calcipotriene.

3. The ointment of claim 1 wherein the corticosteroid is selected from the group consisting of a pharmaceutically acceptable clobetasol salt and a pharmaceutically acceptable betamethasone salt.

4. The ointment of claim 1 wherein the N,N-di($C_1$-$C_8$) alkylamino substituted, ($C_4$-$C_{18}$)alkyl($C_2$-$C_{18}$)carboxylic ester comprises dodecyl 2-(N,Ndimethylamino)-propionate (DDAIP).

5. The ointment of claim 1 wherein the petrolatum earner comprises white petrolatum.

6. The ointment of claim 1 wherein the vitamin D compound is present in the composition at a concentration in the range of about 0.001 to 0.01 percent by weight.

7. The ointment of claim 1 wherein the corticosteroid is present in the composition at a concentration in the range of about 0.01 to 0.1 percent by weight.

8. The ointment of claim 1 wherein the composition includes tocopherol at a concentration in the range of about 0.001 to 0.01 percent by weight.

9. The ointment of claim 1 wherein the N,N-di($C_1$-$C_8$) alkylamino substituted, ($C_4$-$C_{18}$)alkyl($C_2$-$C_{18}$)carboxylic ester is present in the composition at a concentration in the range of about 0.1 to about 5 percent by weight.

10. The ointment of claim 1 wherein the composition includes about 1 to about 10 percent by weight mineral oil.

11. A non-aqueous storage stable ointment suitable for treating psoriasis comprising:
    (a) about 0.001 to about 0.01 percent by weight of a vitamin D compound;
    (b) about 0.01 to about 0.1 percent by weight of a corticosteroid;
    (c) about 0.001 to about 0.01 percent by weight of tocopherol; and
    (d) about 0.1 to about 5 percent by weight of an N,N-di($C_1$-$C_8$) alkylamino substituted, ($C_4$-$C_{18}$) alkyl($C_2$-$C_{18}$) carboxylic ester; in a petrolatum carrier, and optionally containing mineral oil.

12. The ointment of claim 11 wherein the vitamin D derivative compound comprises calcipotriene.

13. The ointment of claim 11 wherein the corticosteroid is selected from the group consisting of clobetasol propionate and betamethasone dipropionate.

14. The ointment of claim 11 wherein the N,N-di($C_1$-$C_8$) alkylamino substituted, ($C_4$-$C_{18}$)alkyl($C_2$-$C_{18}$)carboxylic ester comprises dodecyl 2-(N,N-dimethylamino) propionate (DDAIP).

15. The ointment of claim 11 wherein the petrolatum earner comprises white petrolatum.

16. A non-aqueous storage stable ointment suitable for treating psoriasis comprising:
    (a) about 0.001 to about 0.01 percent by weight of calcipotriene;
    (b) about 0.01 to about 0.1 percent by weight of a corticosteroid selected from the group consisting of clobetasol propionate and betamethasone dipropionate;
    (c) about 0.001 to about 0.01 percent by weight of tocopherol; and
    (d) about 0.1 to about 5 percent by weight of dodecyl 2-(N,N-dimethylamino)-Propionate (DDAIP);
    in a petrolatum carrier, and containing up to about 10 percent by weight mineral oil.

17. The ointment of claim 16 wherein the composition contains about 0.005 percent by weight calcipotriene.

18. The ointment of claim 16 wherein the composition contains about 0.05 percent by weight clobetasol propionate.

19. The ointment of claim 16 wherein the composition contains about 0.064 percent by weight betamethasone dipropionate.

20. The ointment of claim 16 wherein the composition includes about 1 percent by weight DDAIP.

21. The ointment of claim 16 wherein the composition includes about 0.002 percent by weight of tocopherol.

22. The ointment of claim 16 wherein the composition includes about 3 percent by weight mineral oil.

23. The ointment of claim 16 wherein the petrolatum earner comprises white petrolatum.

24. The ointment of claim 16 wherein the composition comprises about 1 percent—about 2.5 percent by weight DDAIP.

25. The ointment of claim 11 wherein the N,N-di($C_1$-$C_8$) alkylamino substituted, ($C_4$-$C_{18}$)alkyl($C_2$-$C_{18}$)carboxylic ester is dodecyl 2-(N,N-dimethylamino) propionate (DDAIP), and the DDAIP is present in the composition in an amount of about 1 percent—about 2.5 percent by weight.

* * * * *